United States Patent
Josephs et al.

(10) Patent No.: US 10,258,631 B2
(45) Date of Patent: Apr. 16, 2019

(54) FORMULATIONS OF TESTOSTERONE AND METHODS OF TREATMENT THEREWITH

(71) Applicants: BOARD OF REGENTS, THE UNIVERSITY OF TEXAS SYSTEM, Austin, TX (US); MEDCARA PHARMACEUTICALS, LLC, Conrad, IA (US)

(72) Inventors: Robert A. Josephs, Austin, TX (US); Craig Herman, Cedar Rapids, IA (US)

(73) Assignees: BOARD OF REGENTS, THE UNIVERSITY OF TEXAS SYSTEM, Austin, TX (US); MEDCARA PHARMACEUTICALS, LLC, Conrad, IA (US)

( * ) Notice: Subject to any disclaimer, the term of this patent is extended or adjusted under 35 U.S.C. 154(b) by 0 days.

(21) Appl. No.: 15/507,246

(22) PCT Filed: Aug. 28, 2015

(86) PCT No.: PCT/US2015/047385
§ 371 (c)(1),
(2) Date: Feb. 27, 2017

(87) PCT Pub. No.: WO2016/033430
PCT Pub. Date: Mar. 3, 2016

(65) Prior Publication Data
US 2017/0281644 A1 Oct. 5, 2017

Related U.S. Application Data

(60) Provisional application No. 62/043,277, filed on Aug. 28, 2014.

(51) Int. Cl.
*A61K 31/5685* (2006.01)
*A61K 45/06* (2006.01)
(Continued)

(52) U.S. Cl.
CPC ........ *A61K 31/5685* (2013.01); *A61K 9/0043* (2013.01); *A61K 9/107* (2013.01);
(Continued)

(58) Field of Classification Search
None
See application file for complete search history.

(56) References Cited

U.S. PATENT DOCUMENTS 5,756,071 A    5/1998  Mattern et al.
6,280,770 B1 *  8/2001  Pather ................. A61K 9/0007
                                                        424/464
(Continued)

FOREIGN PATENT DOCUMENTS

WO    WO 2006/113505     10/2006
WO       2011/129812  *  10/2011

OTHER PUBLICATIONS

Meng et al., International Journal of Nanomedicine 8 (2013): 3051 (Year: 2013).*

(Continued)

*Primary Examiner* — Karl J Puttlitz
(74) *Attorney, Agent, or Firm* — Parker Highlander, PLLC

(57) ABSTRACT

The present disclosure relates to novel pharmaceutical composition for the administration of testosterone or testosterone derivatives. The present disclosure also provides methods of treatment of diseases and disorders associated with fear and anxiety, a decrease in libido, or hypogonadism.

15 Claims, 7 Drawing Sheets

(51) Int. Cl.
| | |
|---|---|
| *A61K 31/568* | (2006.01) |
| *A61K 31/573* | (2006.01) |
| *A61K 9/00* | (2006.01) |
| *A61K 47/14* | (2017.01) |
| *A61K 47/44* | (2017.01) |
| *A61K 9/107* | (2006.01) |

(52) U.S. Cl.
CPC .......... *A61K 31/568* (2013.01); *A61K 31/573* (2013.01); *A61K 45/06* (2013.01); *A61K 47/14* (2013.01); *A61K 47/44* (2013.01)

(56) References Cited

U.S. PATENT DOCUMENTS

| | | | |
|---|---|---|---|
| 2012/0225827 A1* | 9/2012 | Warner | A61K 9/0048 514/20.5 |
| 2013/0040922 A1 | 2/2013 | Kreppner et al. | |
| 2013/0040923 A1* | 2/2013 | Kreppner | A61K 31/568 514/178 |
| 2013/0045958 A1* | 2/2013 | Kreppner | A61K 31/568 514/178 |
| 2013/0059827 A1* | 3/2013 | Kreppner | A61K 31/568 514/178 |
| 2014/0227798 A1 | 8/2014 | Takeuchi et al. | |

OTHER PUBLICATIONS

Cooper et al., American Journal of Psychiatry., vol. 157, No. 11, Nov. 1, 2000 {Nov. 1, 2000), pp. 1884-1884 (Year: 2000).*
Anonymous: "Natesto (testosterone) nasal gel CIII", May 2014 (May 1, 2014) (Year: 2014).*
Banks, et al., Delivery of testosterone to the brain by intranasal administration: comparison to intravenous testosterone, Journal of Drug Targeting, 17(2):91-97, 2009.
Cooper and Ritchie, "Testosterone Replacement Therapy for Anxiety," Am. J. Psychiatry, 157(11):1884, 2000.
Davison, et al., Pharmacokinetics and acute safety of inhaled testosterone in postmenopausal women, The Journal of Clinical Pharmacology, 45(2):177-184, 2005.
Giltay, et al., Salivary testosterone: Associations with depression, anxiety disorders, and antidepressant use in a large cohort study, Journal of Psychosomatic Research, 72(3):205-213, 2012.
Goel and Bale, "Examining the intersection of sex and stress in modeling neuropsychiatric disorders", *J Neuroendocrinol.*, 24(4):415-420, 2009.
Goel and Bale, "Organizational and Activational Effects of Testosterone on Masculinization of Female Physiology and Behavioral Stress Responses", *Endocrinology*, 149(12):6399-6405, 2008.
Hermans et al., "Exogenous testosterone enhances responsiveness to social threat in the neural circuitry of social aggression in humans", *Biological Psychiatry*, 63(3):263-270, 2008.

International Preliminary Report on Patentability issued in International Application No. PCT/US2015/047385, dated Mar. 9, 2017.
International Search Report and Written Opinion issued in International Application No. PCT/US2015/047385, dated Jan. 28, 2016.
Karlovic et al., "Serum testosterone concentration in combat-related chronic posttraumatic stress disorder", *Neuropsychobiology*, 65(2):90-5, 2012.
Ko et al., "Emulsion formulations of testosterone for nasal administration", *J. Microencapsulation*, 15(2):197-205, 1998.
Mason et al., "Serum testosterone levels in post traumatic stress disorder inpatients", *Journal of Traumatic Stress*, 3(3):449-457, 1990.
Miskovic et al., "Changes in EEG Cross-Frequency Coupling During Cognitive Behavioral Therapy for Social Anxiety Disorder", *Psychological Science*, 22:507-516, 2011.
Montgomery, et al., Effect of oestrogen and testosterone implants on psychological disorders in the climacteric, The Lancet, 329(8528):297-299, 1987.
Perez-Rodriguez et al., "Lack of Association between Testosterone and Suicide Attempts", *Neuropsychobiology*, 63:125-130, 2011.
Pope et al., "Testosterone Gel Supplementation for Men with Refractory Depression: A Randomized, Placebo-Controlled Trial", *Am. J. Psychiatry*, 160:105-111, 2003.
Reijnen, et al., The Effect of Deployment to a Combat-zone on Testosterone Levels and the Association with the Development of Posttraumatic Stress Symptoms; a Longitudinal Prospective Dutch Military Cohort Study, Psychoneuroendocrinology, 2014.
Rolf, C., et al., Pharmacokinetics of a new transdermal testosterone gel in gonadotrophin-suppressed normal men, European Journal of Endocrinology, 146(5):673-679, 2002.
Sladky et al., "Increased Neural Habituation in the Amygdala and the Orbitofrontal Cortex in Social Anxiety Disorder Revealed by fMRI", *PLOS ONE*, 7(11):1-9, 2012.
Tuiten et al., "Time Course of Effects of Testosterone Administration on Sexual Arousal in Women", *Arch Gen Psychiatry*, 57:149-153, 2000.
Van Honk et al., "Testosterone reduces unconscious fear but not consciously experienced anxiety: Implications for the disorders of fear and anxiety", *Biological Psychiatry*, 58(3):218-225, 2005.
Wirth and Schultheiss, "Basal testosterone moderates responses to anger faces in humans", *Psychology and Behavior*, 90:496-505, 2007.
"Natesto (testosterone) nasal gel CIII", dated May 1, 2014, from www.accessdata.fda.gov/drugstatfda_docs/label/201/205488s0001bl.pdf (retrieved on Jan. 19, 2018).
Extended European Search Report issued in European Application No. 15834874.8, dated Feb. 1, 2018.
Meng, et al. "Enhanced transdermal bioavailability of testosterone propionate via surfactant-modified ethosomes." *International journal of nanomedicine* 8 (2013): 3051.
Shoskes, et al., "Pharmacology of testosterone replacement therapy preparations." *Translational andrology and urology* 5.6 (2016): 834.

* cited by examiner

FORMULATIONS OF TESTOSTERONE AND METHODS OF TREATMENT THEREWITH

This application is a national phase application under 35 U.S.C. § 371 of International Application No. PCT/US2015/047385, filed Aug. 28, 2015, which claims the benefit of U.S. Provisional Patent Application No. 62/043,277, filed Aug. 28, 2014, the entirety of which are incorporated herein by reference.

BACKGROUND OF THE INVENTION

1. Field of the Invention

The present disclosure relates generally to the fields of medicine, pharmaceutical agents, hypogonadism disorders, and disorders associated with fear or anxiety. More particularly, it relates to compositions of testosterone which can be used to treat disorders associated with fear and anxiety, erectile dysfunction, sexual dysfunction, or decreased libido.

2. Description of Related Art

Administration of testosterone is difficult as the hormone is not particular amenable to oral administration. Typically, testosterone is administered intravenously, intramuscularly, or transdermally. All of these methods have drawbacks including repeated use of syringes, cross contamination, or decreased amounts of the biological active compound.

Several nasal formulations for the administration of testosterone have been developed including by Trimel Pharmaceuticals (PCT Publication WO 2006/113505, U.S. Pat. No. 5,756,071, US Patent Publication 2013/059827, 2013/045958, 2013/0040923, and 2013/0040922). Intranasal administration of testosterone has been shown to increase testosterone concentrations dramatically and rapidly—increasing concentrations from baseline (mean of 2.5 pmol/L) to maximum (mean of 168.2 pmol/L) 1 to 2 minutes after dosing (Davison et al., 2005). Transdermal gel application, on the other hand, is a slower and considerably less efficient administration method. Increasing concentrations to maximum levels using transdermal gel has been reported to take 10 days, and includes daily gel applications (mean of 2.3 nmol/L on day 1 to a mean of 14.6 nmol/L on day 10 according to Rolf et al., 2002). Additionally, nasally administered testosterone has been shown to have a greater concentration in the brain than testosterone administered through intravenous injection, with whole brain levels of testosterone reported to be twice as high after intranasal administration compared to intravenous administration (Banks et al., 2009). These nasal formulations are developed using castor oil to disperse the active testosterone or testosterone ester. Castor oil facilitates uptake of compounds through the mucosa membranes but unfortunately is not very selective in that uptake. An aqueous based formulation can prevent much of the cross contamination and irritation exhibited by castor oil based formulations. Therefore, the development of new testosterone formulations is of therapeutic importance.

At the most general level, anxiety disorders (which include post-traumatic stress disorder) are thought to be caused by an inability to correctly regulate the brain's response to fear and danger in the environment (Beck, et al., 2005). Testosterone has been shown to play a critical role in the body's response to fear and anxiety (van Honk, et al., 2005 and Hermans, 2008), and thus, perhaps not surprisingly, low testosterone levels have been implicated as a risk factor for the development of post-traumatic stress disorder by Mason, et al. (1990), Karlovic, et al. (2012), and Reijnen, et al. (2014). Because modulation of testosterone levels is believed to play an important role in the etiology of anxiety disorders (Giltay et al., 2012; Montgomery et al., 1987; van Honk et al., 2005), new and more effective methods of delivering testosterone are needed which will increase bioavailable testosterone.

SUMMARY OF THE INVENTION

In some aspects, the present disclosure provides pharmaceutical compositions comprising the following components dissolved in an aqueous solution:

(A) a compound of the formula:

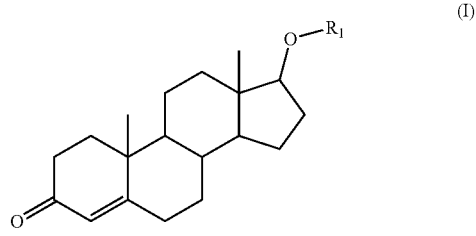

wherein: $R_1$ is hydrogen, acyl$_{(C \leq 12)}$, or substituted acyl$_{(C \leq 12)}$;

(B) a first additive substantially comprised of a compound of the formula:

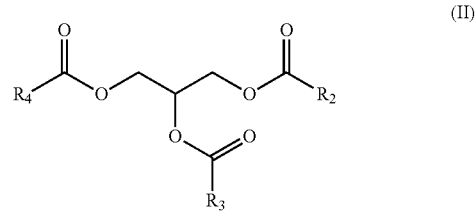

wherein: $R_2$, $R_3$, and $R_4$ are each independently selected from alkyl$_{(C \leq 12)}$, alkenyl$_{(C \leq 12)}$, alkynyl$_{(C \leq 12)}$, or a substituted version of any of these groups; and (C) a second additive substantially comprised of a compound of the formula:

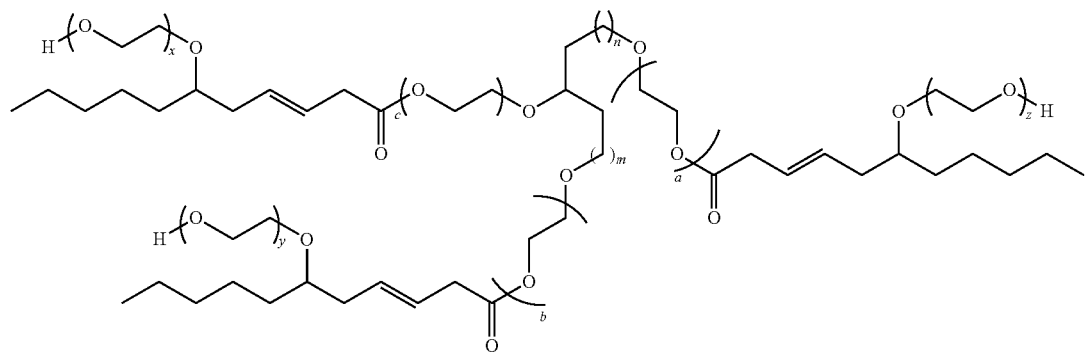

(III)

wherein: x, y, z, a, b, and c are each independently a number selected from 0-40 provided that at least one of x, y, z, a, b, or c is not 0; and m and n are each independently selected from 0, 1, or 2. In some embodiments, $R_1$ is $acyl_{(C \leq 12)}$. In some embodiments, $R_1$ is

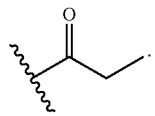 [SMILES: *C(=O)CC]

In some embodiments, $R_2$ is $alkyl_{(C \leq 12)}$ or substituted $alkyl_{(C \leq 12)}$. In some embodiments, $R_2$ is $alkyl_{(C6-12)}$. In some embodiments, $R_2$ is octyl or decyl. In some embodiments, $R_3$ is $alkyl_{(C \leq 12)}$ or substituted $alkyl_{(C \leq 12)}$. In some embodiments, $R_3$ is $alkyl_{(C6-12)}$. In some embodiments, $R_3$ is octyl or decyl. In some embodiments, $R_4$ is $alkyl_{(C \leq 12)}$ or substituted $alkyl_{(C \leq 12)}$. In some embodiments, $R_4$ is $alkyl_{(C6-12)}$. In some embodiments, $R_4$ is octyl or decyl. In some embodiments, one of $R_2$, $R_3$, and $R_4$ is decyl and the other two of $R_2$, $R_3$, and $R_4$ are octyl. In some embodiments, m is 0. In other embodiments, m is 1. In some embodiments, x, y, and z are 0. In other embodiments, a, b, and c are 0. In some embodiments, the compositions comprise between 0.1% to about 5% by weight of component (A). In some embodiments, the compositions comprise between about 1% to about 3% by weight of component (A). In some embodiments, the compositions comprise about 1.2% by weight of component (A). In other embodiments, the compositions comprise about 2.2% by weight of component (A). In some embodiments, the compositions comprise between about 1% to about 10% by weight of component (B). In some embodiments, the compositions comprise between about 3% to about 7% by weight of component (B). In some embodiments, the compositions comprise from about 4.5% to about 5.5% by weight of component (B). In other embodiments, the compositions comprise between about 10% to about 20% by weight of component (B). In some embodiments, the compositions comprise between about 12% to about 16% by weight of component (B). In some embodiments, the compositions comprise from about 14% to about 15% by weight of component (B). In some embodiments, the compositions comprise about 15% to about 40% by weight of component (C). In some embodiments, the compositions comprise about 15% to about 30% by weight of component (C). In some embodiments, the compositions comprise from about 22% to about 26% by weight of component (C). In some embodiments, the compositions comprise from about 50% to about 90% by weight of water. In some embodiments, the compositions comprise from about 60% to about 80% by weight of water. In some embodiments, the compositions comprise from about 68% to about 72% by weight of water. In other embodiments, the compositions comprise from about 50% to about 70% by weight of water. In some embodiments, the compositions comprise from about 55% to about 60% by weight of water. In some embodiments, the compositions are formulated for administration nasally. In some embodiments, the compositions further comprise a preservative. In some embodiments, the composition comprises from about 0.01% by weight to about 5% by weight of the preservative. In some embodiments, the composition is sterilized. In some embodiments, the composition is sterilized by filtration. In some embodiments, the composition is sterilized by filtration with a Tuffryn® filter. In some embodiments, the Tuffryn® filter is a 0.22 micron Tuffryn® filter.

In another aspect, the present disclosure provides pharmaceutical compositions comprising a testosterone $ester_{(C \leq 12)}$, water, and a first additive. In some embodiments, the testosterone $ester_{(C \leq 12)}$ is testosterone propionate. In some embodiments, the water is distilled water. In some embodiments, the first additive is a reaction mixture from the reaction of castor oil with ethylene oxide. In some embodiments, the reaction comprises a molar ratio of ethylene oxide to castor oil of about 35:1. In some embodiments, the first additive is a Cremophor® composition. In some embodiments, the first additive is Cremophor® 35. In some embodiments, the compositions further comprise a second additive. In some embodiments, the second additive is a caprylic/capric triglyceride. In some embodiments, the second additive is a dicaprylic acid and monocarpic triglyceride. In some embodiments, the second additive is a Neobee® medium chain triglyceride composition. In some embodiments, the second additive is Neobee® M-5. In some embodiments, the second additive comprises from about 1% to about 10% by weight of the composition. In some embodiments, the second additive comprises from about 4.5% to about 5.5% by weight of the composition. In other embodiments, the second additive comprises from about 10% to about 20% by weight of the composition. In some embodiments, the second additive comprises from about 14% to about 16% by weight of the composition. In some embodiments, the testosterone $ester_{(C \leq 12)}$ comprises from about 0.1% to about 5% by weight of the composition. In some embodiments, the testosterone ester$_{(C≤12)}$ is about 1.2% by weight of the composition. In other embodiments, the testosterone ester$_{(C≤12)}$ is about 2.2% by weight of the composition. In some embodiments, the water comprises from about 65% to about 75% by weight of the composition. In some embodiments, the water is from about 68% to about 72% by weight of the composition. In other embodiments, the water comprises from about 55% to about 65% by weight of the composition. In some embodiments, the water comprises from about 57% to about 60% by weight of the composition. In some embodiments, the first additive comprises from about 15% to about 25% by weight of the composition. In some embodiments, the first additive is from about 22% to about 26% by weight of the composition. In some embodiments, the composition is formulated for administration nasally. In some embodiments, the composition further comprises a preservative. In some embodiments, the compositions comprise from about 0.01% by weight to about 5% by weight of the preservative. In some embodiments, the compositions are sterilized. In some embodiments, the compositions are sterilized by filtration. In some embodiments, the compositions are sterilized by filtration with a Tuffryn® filter. In other embodiments, the Tuffryn® filter is a 0.22 micron Tuffryn® filter.

In yet another aspect, the present disclosure provides a pharmaceutical compositions comprising about 1.2% by weight testosterone propionate, about 71.6% by weight distilled water, about 4.9% by weight Neobee® M-5, and about 22.3% by weight Cremophor® EL. In some embodiments, the compositions are formulated for administration nasally. In some embodiments, the compositions further comprise a preservative. In some embodiments, the compositions comprise from about 0.01% by weight to about 5% by weight of the preservative. In some embodiments, the compositions are sterilized. In some embodiments, the compositions are sterilized by filtration. In some embodiments, the compositions are sterilized by filtration with a Tuffryn® filter. In some embodiments, the Tuffryn® filter is a 0.22 micron Tuffryn® filter.

In yet another aspect, the present disclosure provides pharmaceutical compositions comprising about 2.2% by weight testosterone propionate, about 58.7% by weight distilled water, about 14.3% by weight Neobee® M-5, and about 24.8% by weight Cremophor® EL. In some embodiments, the compositions are formulated for administration nasally. In some embodiments, the compositions further comprise a preservative. In some embodiments, the compositions comprise from about 0.01% by weight to about 5% by weight of the preservative. In some embodiments, the compositions are sterilized. In some embodiments, the compositions are sterilized by filtration. In some embodiments, the compositions are sterilized by filtration with a Tuffryn® filter. In some embodiments, the Tuffryn® filter is a 0.22 micron Tuffryn® filter.

In another aspect, the present disclosure provides methods of treating a disease or disorder in a patient in need thereof comprising nasally administering to the patient a therapeutically effective amount of testosterone. In some embodiments, the testosterone is formulated or comprised in a composition of testosterone described herein. In some embodiments, the disease or disorder is a disease or disorder associated with fear and anxiety. In some embodiments, the disease or disorder is a disorder of the fear processing system. In some embodiments, the disease or disorder is anxiety disorder, major depressive disorder, post-traumatic stress disorder, generalized anxiety disorder, panic disorder, social phobia, non-social phobia, social anxiety disorder, or obsessive compulsive disorder. In some embodiments, the disease or disorder is post-traumatic stress disorder. In other embodiments, the disease or disorder is major depressive disorder. In other embodiments, the disease or disorder is an anxiety disorder. In other embodiments, the disease or disorder is a generalized anxiety disorder. In other embodiments, the disease or disorder is a panic disorder. In other embodiments, the disease or disorder is a social phobia. In other embodiments, the disease or disorder is a non-social phobia. In other embodiments, the disease or disorder is a social anxiety disorder. In some embodiments, the disease or disorder is an obsessive compulsive disorder. In some embodiments, the patient is female. In other embodiments, the patient is male. In some embodiments, the methods comprise administering a second therapeutic agent. In some embodiments, the second therapeutic agent is a second pharmaceutical agent, psychotherapy, or cognitive behavioral therapy. In some embodiments, the second pharmaceutical agent is cortisol. In some embodiments, the second pharmaceutical agent is a compound which modulates the patient's cortisol levels. In some embodiments, the methods lead to the reduction of one or more symptoms of an anxiety or fear related disease or disorder. In other embodiments, the disease or disorder is associated with a deficiency in testosterone. In some embodiments, the deficiency in testosterone leads to decreased libido. In some embodiments, the decreased libido is self reported. In some embodiments, the decreased libido results in the patient having comparatively low or no libido. In some embodiments, the decreased libido is in a male or female patient. In some embodiments, the patient is female. In other embodiments, the patient is male. In some embodiments, the disease or disorder is associated with hypogonadism. In other embodiments, the patient has erectile dysfunction. In some embodiments, the patient is a male. In some embodiments, the patient is human. In some embodiments, the therapeutically effective amount is administered in a single dose per day. In other embodiments, the therapeutically effective amount is administered in two or more doses per day. In other embodiments, the therapeutically effective amount is administered as needed. In some embodiments, the patient is treated at least a second time. In some embodiments, the patient is treated over a period of 1 week to 6 months. In other embodiments, the patient is treated for a period of 6 months to 5 years.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used herein, the term "substantially" is used to represent a composition comprising at least 90% of the desired compound. The term "more substantially" is used to represent a composition comprising at least 95% of the desired compound. The term "essentially" is used to represent a composition comprising at least 97% of the desired compound. Conversely, the term "substantially free of" or "substantially free" in terms of a specified component, is used herein to mean that none of the specified component has been purposefully formulated into a composition and/or is present only as a contaminant or in trace amounts. The total amount of all containments, by-products, and other material is present in that composition in an amount less than 5%. The term "more substantially free of" or "more substantially free" is used to represent that the composition contains less than 3% of the specific component. The term "essentially free of" or "essentially free" contains less than 2% of the specific component.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description and examples provided herewith.

DESCRIPTION OF ILLUSTRATIVE EMBODIMENTS

Figure 1:
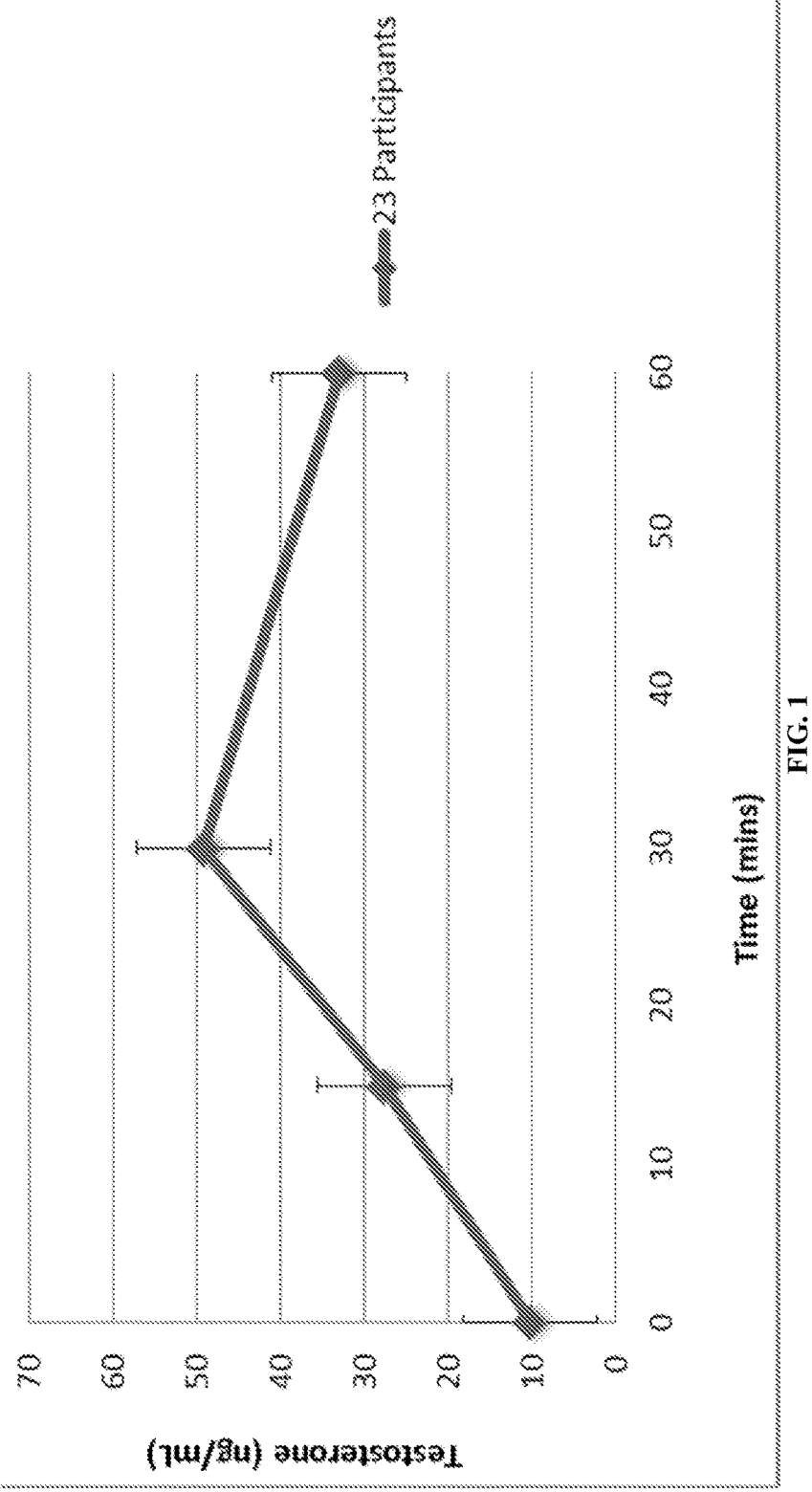
FIG. 1—shows the pharmacokinetic profile of the aqueous 2.2% testosterone spray described herein. The pharmacokinetic profile shows that the maximum concentration of free testosterone is shown at approximately 30 minutes after administration.
Figure 2:
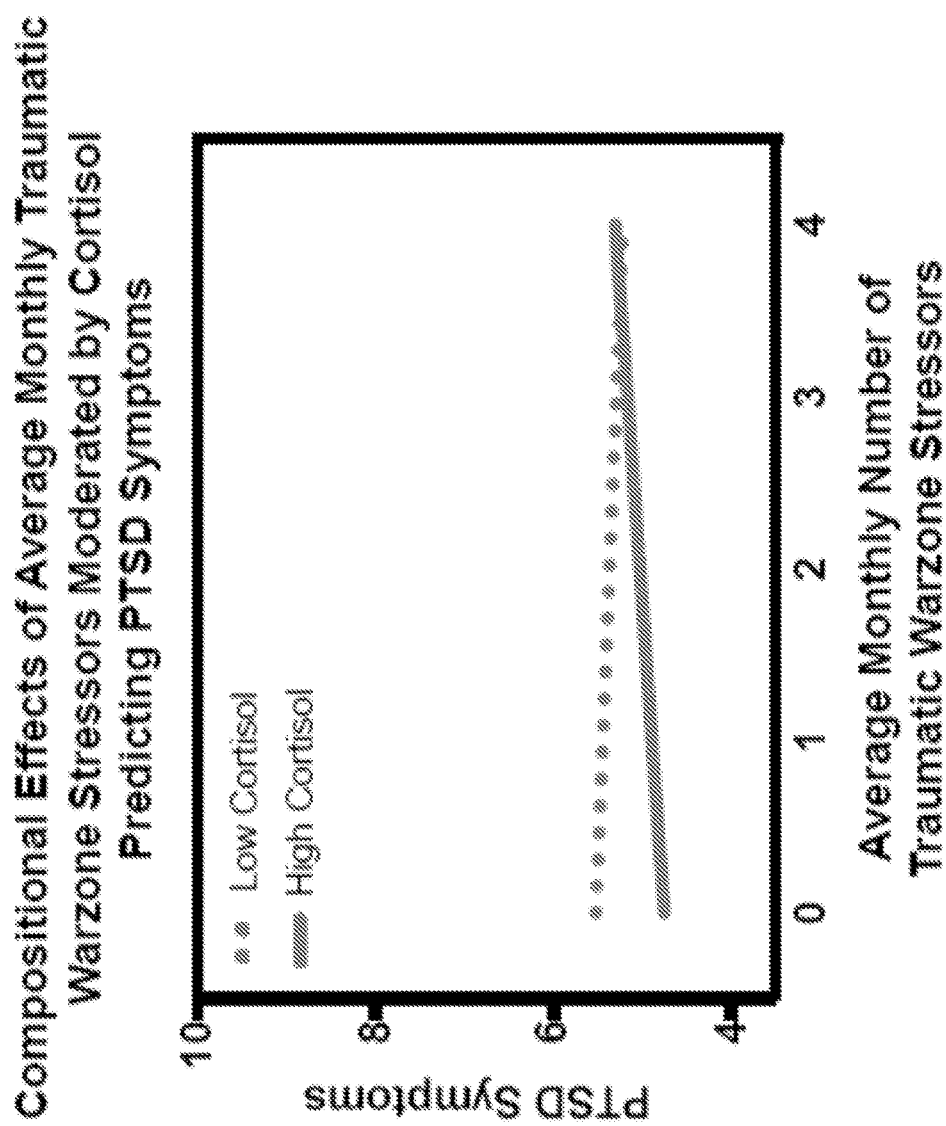
FIG. 2—shows the correlation of PTSD symptoms exhibited as a function of average monthly numbers of traumatic warzone stressors based upon the patients' cortisol levels. The trend lines in the graph show the average number of PTSD symptoms for patients with high cortisol levels and low cortisol levels based upon the average number of traumatic warzone stressors.
Figure 3:
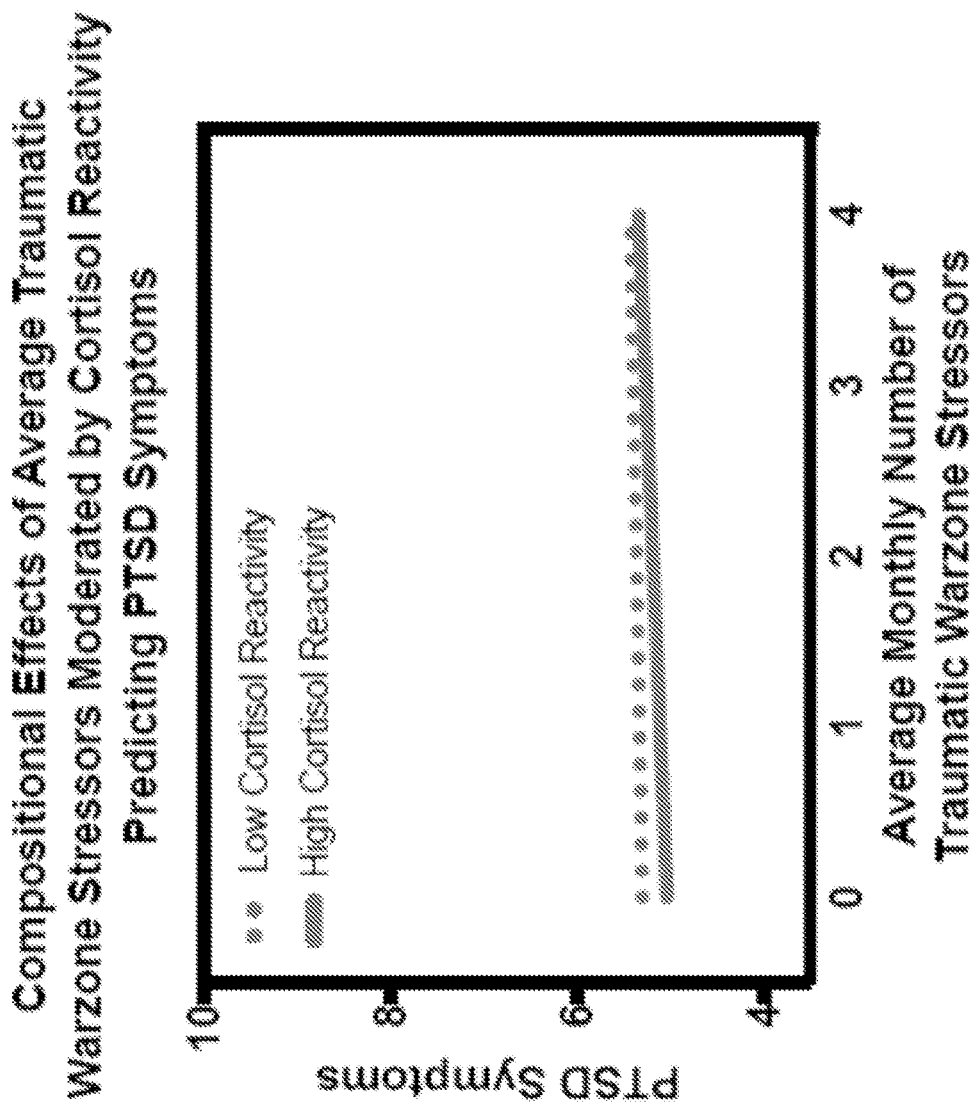
FIG. 3—shows the correlation of PTSD symptoms exhibited as a function of average monthly numbers of traumatic warzone stressors based upon the patients' cortisol reactivity. The trend lines in the graph show the average number of PTSD symptoms for patients with high cortisol reactivity and low cortisol reactivity based upon the average number of traumatic warzone stressors.
Figure 4:
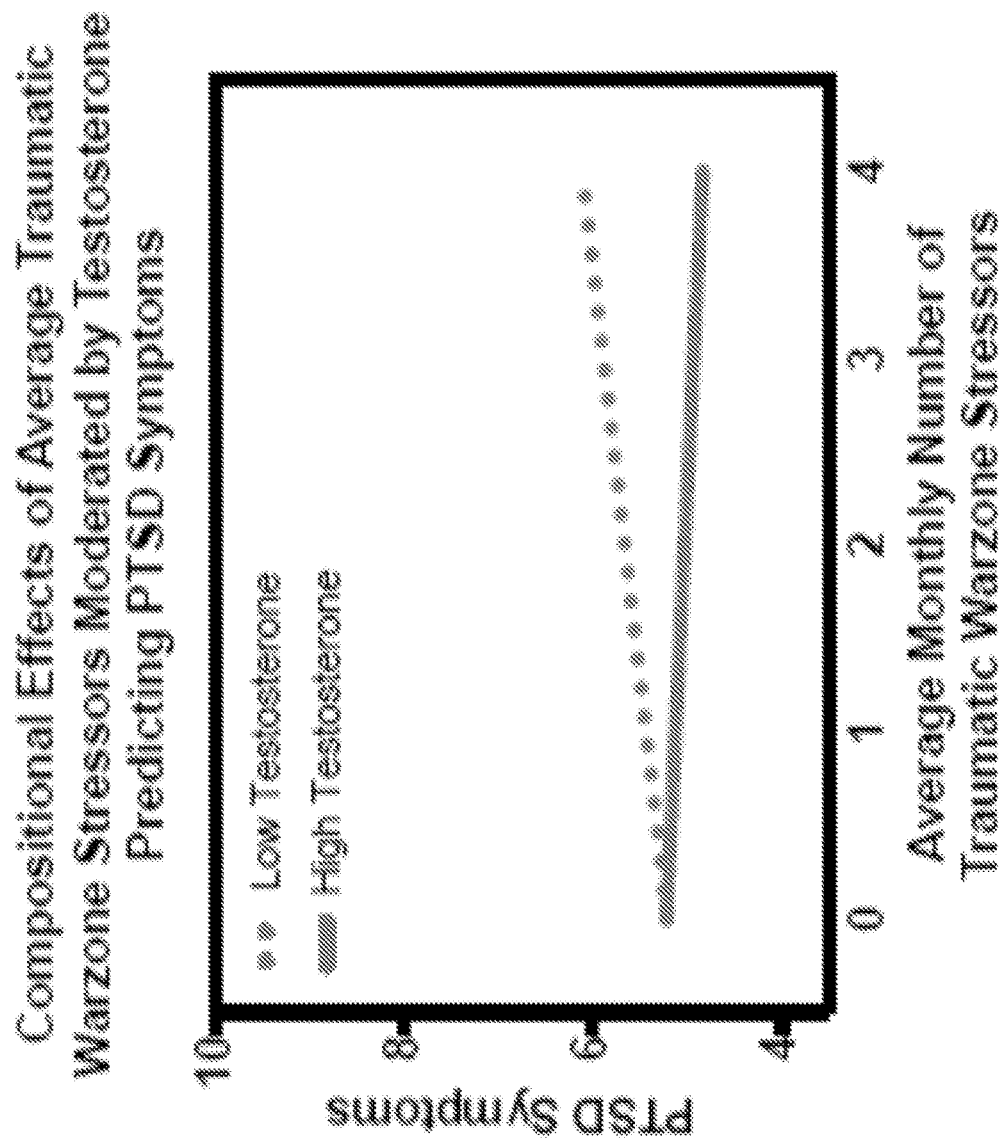
FIG. 4—shows the correlation of PTSD symptoms exhibited as a function of average monthly numbers of traumatic warzone stressors based upon the patients' testosterone levels. The trend lines in the graph show the average number of PTSD symptoms for patients with high testosterone levels and low testosterone levels based upon the average number of traumatic warzone stressors.
Figure 5:
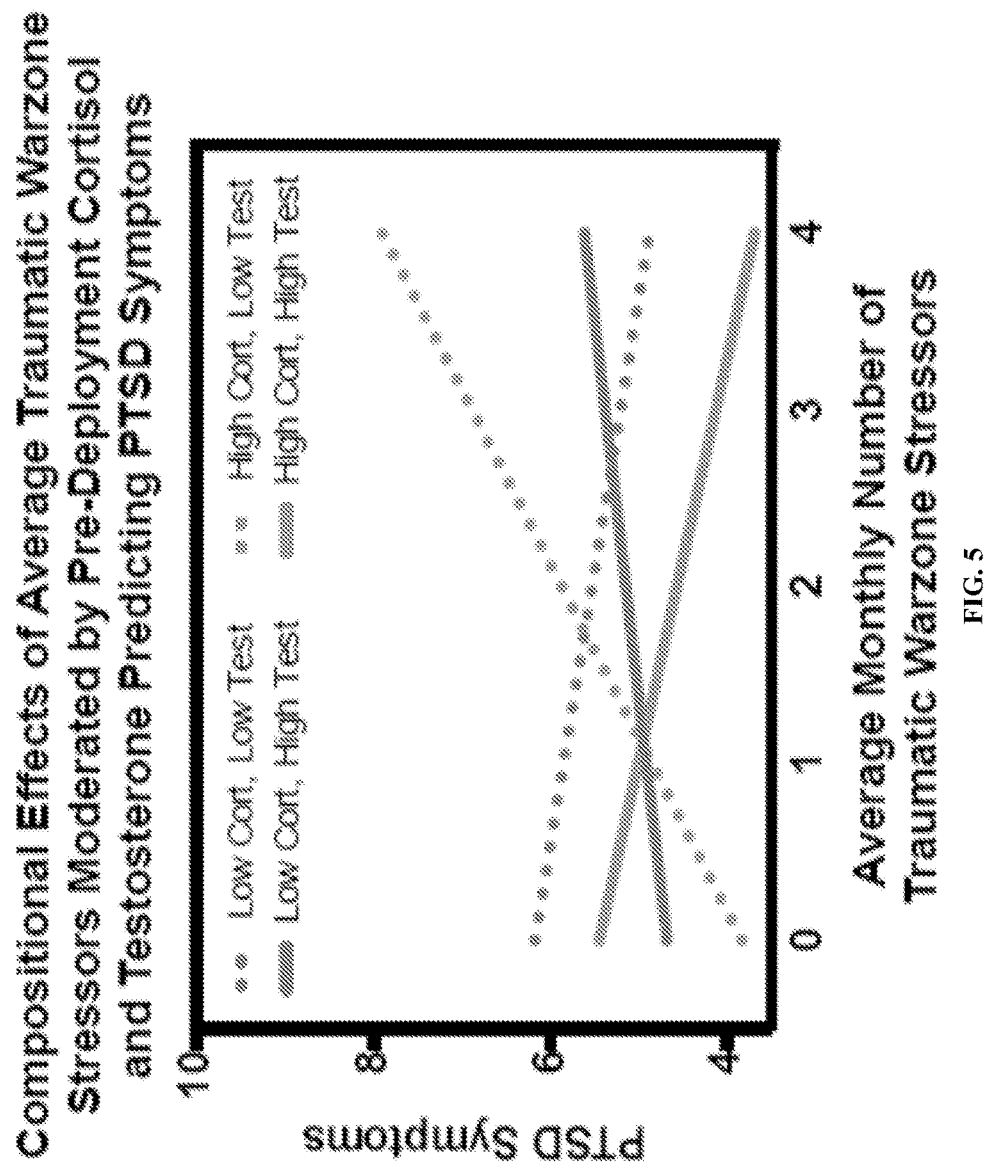
FIG. 5—shows the correlation of PTSD symptoms exhibited as a function of average monthly numbers of traumatic warzone stressors based upon the patients' cortisol levels and testosterone levels. The trend lines in the graph show the average number of PTSD symptoms for patients with combinations of high or low cortisol levels and high or low testosterone levels based upon the average number of traumatic warzone stressors.

The present disclosure provides new compositions for the administration of testosterone to a patient. In some embodiments, the composition of the administration of testosterone is administered nasally. Without being bound by theory, administration of the testosterone nasally allows the testosterone to rapidly reach the blood stream and increases the amount of testosterone which reaches the brain. In some aspects, the present disclosure provides methods of treating diseases and disorders with testosterone including hypogonadism including but not limited to decreased libido, sexual dysfunction, and erectile dysfunction and fear and anxiety disorders including but not limited to post traumatic stress disorder or social anxiety disorder.

A. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro"

means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfate" means —S(O)₂OH—; "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

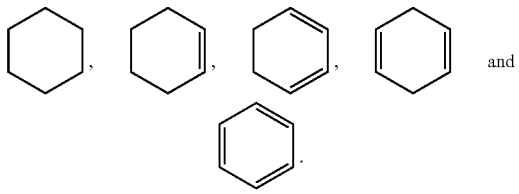

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫶⫶⫶" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

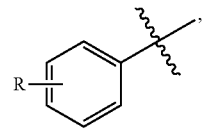

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

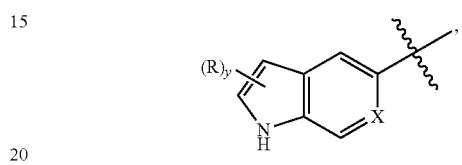

then R may replace any hydrogen atom attached to any of the ring atoms of either of the fused rings unless specified otherwise. Replaceable hydrogen atoms include depicted hydrogens (e.g., the hydrogen atom attached to the nitrogen atom in the formula above), implied hydrogens (e.g., a hydrogen atom of the formula above that is not shown but understood to be present), expressly defined hydrogen atoms, and optional hydrogen atoms whose presence depends on the identity of a ring atom (e.g., a hydrogen atom attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl.

The term "alkenyl" when used without the "substituted" modifier refers to an monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to an monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

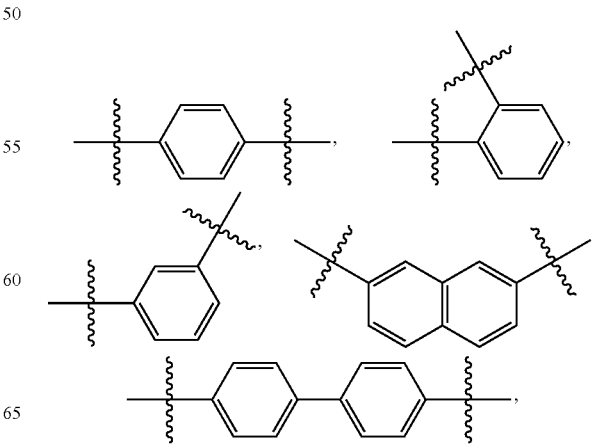

-continued

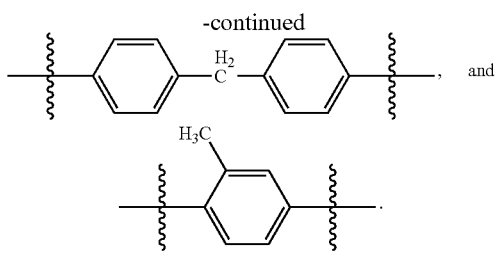

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —SH, —OCH$_3$, —OCH$_2$CH$_3$, —NHCH$_3$, —NHCH$_2$CH$_3$, —N(CH$_3$)$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The composition "Neobee® M-5" is a medium chain triglyceride with the CAS Registry No. 73398-61-5. The composition "Cremophor EL®" or "Kolliphor EL" is a polyethoxylated castor oil with the CAS Registry No. 61791-12-6. The syringe filter "Tuffryn®" is a hydrophilic polysulfone membrane filter.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As used herein, "PEG" is polyethylene glycol with a repeating unit of —(OCH$_2$CH$_2$)$_n$OH, wherein n is the number of repeats. A molecule which has been "PEGylated" or contains "one or more PEG groups" is a molecule which has been covalently linked to a polyethylene glycol group as that group is described above.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an biologically active compound according to the present disclosure. The prodrug itself may or may not also have activity with respect to a given target protein.

For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "testosterone ester" as used in the context of this application is a derivative of testosterone comprising at least a substitution on the hydroxyl group on the cyclopentyl ring of the steroid core with an acyl functional group or a substituted acyl functional group as those functional groups are defined above. When a carbon limit is assigned to a testosterone ester, the carbon limit is relative only to the carbon atoms on the acyl substitution. The terms "testosterone", "testosterone ester", or "testosterone derivative" are used interchangeably unless specifically noted otherwise.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. Fear and Anxiety Related Diseases and Disorders

Fear and anxiety related diseases and disorders are associated with the dysregulation of the fear processing centers in the brain. In particular, testosterone or derivatives thereof or the formulations of the present disclosure may be used to treat a fear or anxiety related disease or disorder. Without being bound by theory, the treatment of these diseases and disorder with an agent that modulates the brain's response to fear is effective in treating these diseases and disorders. In general, phobias such as social phobias and non-social phobias are centered around the fear of a particular thing. In a non-limiting example, non-social phobias include arachnophobia, hemophobia, or chemophobia and related to a fear of specific object such as spiders, blood, and chemicals, respectively. Social phobia, on the other hand, is a fear of either a generalized or specific social situation. In a few non-limiting examples, social phobias can be associated with such generalized social situations as attending an event with a crowd, conversing with strangers, or meeting new people at a club. On the other hand, specific social phobias can include fear of public speaking, fear of conversing with a particular group such as the opposite gender, or a fear or interacting with a specific group of people such as dentist or doctors in a few non-limiting examples.

Furthermore, fear or anxiety related diseases or disorders include panic disorders which are associated with fear of a particular situation or stimulus that is present during an initial attack. Panic disorders are noted by the rapid and repeated onset of fear, in some cases, debilitating fear, which can impact an individuals ability to work and can last anywhere from minutes to hours. Additionally, the patient tends to have fear of having another attack. Treatment of these diseases or disorders with compounds that can modulate the fear are potentially therapeutically important treatment options. Additionally, generalized anxiety disorder is when a patient exhibits anxiety towards a routine worry which cannot be resolved even when the patient no longer has a rational reason to worry.

Additionally, people can become fixed on patterns and routines such that these become an obsession. When the individual feels compelled to perform these activities as a means of reducing anxiety—even though the activities interfere with the individual's daily life—the individual may be diagnosed with obsessive compulsive disorder. Such anxiety-driven compulsions in an individual can be modulated by changing the fear response of the individual.

Finally, post-traumatic stress disorder (PTSD) results when the body's fight or flight systems become dysregulated from exposure to actual or imagined fearful stimuli. In individuals with PTSD, the individual continues to react as if the fearful stimuli are present even after the stimuli are removed. Traditionally, the disorder is most associated with war veterans but can occur after the individual experiences any traumatic event or someone close to the individual experiences a traumatic event. Often, these events are associated with a threat of bodily harm.

C. Hypogonadism and Decreased Sexual Desire

In some aspects of the present disclosure, testosterone may be used to treat males with clinically low testosterone levels—hypogonadism—or decreased libido in either males or females. Although both males and females can present with symptoms of hypogonadism, it is typically diagnosed only in males. In males, hypogonadism is a physiological condition in which the body does not produce enough testosterone. Hypogonadism can be acquired or congenital and administration of testosterone can be efficacious in treating both forms. In some embodiments, the hypogonadism can be treated with testosterone replacement therapy. Male hypogonadism is associated with several different complications including, but not limited to decreased sex drive, fatigue, muscle loss or weakness, erectile dysfunction, osteoporosis, or infertility. Additionally, low testosterone levels have been implicated in decreased lifespan in males. Although testosterone levels decrease with age, in some embodiments, the sub-optimal levels of testosterone may be treated with nasal administration of testosterone. In some embodiments, the treatment with testosterone nasally is in conjunction with another method of administering testosterone on a long term basis such as through a transdermal patch, injections, or a topical administration.

Additionally, in some embodiments, testosterone may be used to treat women with decreased sexual desire or sex drive. Single-dose administration of testosterone has been shown to increase subjective sexual desire, genital responsiveness, and genital arousal in women when the testosterone has been sublingually. In some embodiments, the women being treated have a clinically diagnosed low level of sexual desire compared to the average population. In some embodiments, the administration of testosterone increases the sexual desire. In some embodiments, the testosterone is administered to women who are postmenopausal or who use hormonal contraceptives. Additionally, in some embodiments, testosterone is administered to women who have low levels of energy or to combat a decrease in bone density or muscle mass.

D. Nasal Pharmaceutical Formulations and Routes of Administration

In some aspects of the present disclosure, the testosterone is formulated for administration nasally. Nasal formulations comprise the pharmaceutically active compound and at least one excipient which allows for the aerosolization of the compound. Ideally, the compound in combination with the excipient will produce an aerosol without leading to a loss of clarity or precipitation of the pharmaceutically active compound. In some embodiments, the composition of the present disclosure further comprises a preservative agent. In some embodiments, the preservative agent comprises from about 0.01% to about 5% of the solution by weight. Preservative agents are well known to those of skill in the art and include but are not limited to benzalkonium salts, thimerosal, sodium or potassium phosphate, phenylcarbinol, benzyl alcohol, sodium EDTA, providone, iodine, and sodium silicoaluminate. In some embodiments, the nasal formulation of a pharmaceutical active compound such as testosterone should not be irritating to the nasal lining or mucosal membranes. In some embodiments, the aqueous formulations for nasal administration are more efficacious, more readily absorbed, or faster drying than other compositions. Additionally, it is envisioned that testosterone and these testosterone compositions described herein can also be administered in other manners such as sublingually if that method is tolerated by the patient.

The nasal formulation is an aqueous formulation which contains at least 10% water. In some embodiments, the formulation comprises at least 25% water. In some embodiments, the formulation comprises at least 50% water. In some embodiments, the formulation comprises at least 10%, 15%, 20%, 25%, 30%, 35%, 40%, 45%, or 50%. In some aspects, the formulations and compositions provided herein comprise one or more hydrophobic additives. The hydrophobic additives may be triglyceride compounds. In some embodiments, the triglyceride compounds have medium length fatty acid chains with a carbon length of 6-14 carbon atoms. Other hydrophobic additives that may be used include derivatives of triglycerides which contain one or more PEGylated portions of the molecule. In some embodiments, the triglyceride is contains one or more polyethylene glycol groups on the fatty acid. In other embodiments, the polyethylene glycol group is incorporated between the glyceride and the fatty acid. Some non-limiting examples of such compounds include compounds of the formula:

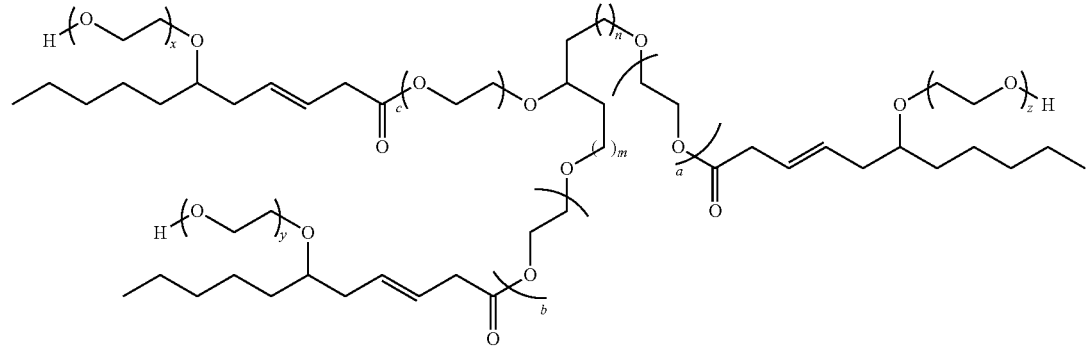

wherein: x, y, z, a, b, and c are each independently a number selected from 0-40 provided that at least one of x, y, z, a, b, or c is not 0; and m and n are each independently selected from 0, 1, or 2. In some embodiments, x, y, and z are each 0. In other embodiments, a, b, and c are each 0. In some embodiments, m is 0 or 1. In some embodiments, m is 0. In some embodiments, n is 0 or 1. In some embodiments, n is 0. In some embodiments, Cremophor® 35 is an example of PEGylated triglyceride. In some embodiments, the composition or formulation consists essentially of testosterone, water, and one or more hydrophobic additives. In some embodiments, the composition or formulation consists essentially of testosterone, water, and two hydrophobic additives.

In some aspects, the compositions of the present disclosure may be faster acting than compositions described in the prior art. The pharmacokinetic aspects of the present compositions may be used to achieve a high serum concentration of free testosterone within a short period of time after administration. In some embodiments, the high serum concentration of testosterone may also be reduced within a relatively short time window. The high concentration of testosterone may be a serum total testosterone concentration of greater than 8 ng/mL within 45 minutes of administration. In some embodiments, the total serum testosterone concentration is greater than 10 ng/mL within 45 minutes of administration. In some embodiments, the high serum concentration of testosterone is achieved within 30 minutes of administration. The high concentration of testosterone may be achieved with in 15, 20, 22, 24, 26, 28, 30, 32, 34, 36, 38, 40, or 45 minutes, or any range derivable therein of administration. Conversely, the serum testosterone concentration may also be reduced quickly after administration. In some embodiments, the total serum testosterone concentration is reduced by more than 15% within 90 minutes of administration. The total serum testosterone concentration may be reduced by more than 25% within 90 minutes of administration. In some embodiments, the total serum testosterone concentration is reduced by more than 15% within 60 minutes of administration. The total serum testosterone concentration may be reduced by more than 25% within 60, 65, 70, 75, 80, 85, or 90 minutes, or any range derivable therein of administration. Without wishing to be bound by any theory, it is believed that the administration of testosterone in such a manner that it achieves high serum concentrations within about 45 minutes after administration but the serum concentration is quickly reduced within 1, 2, 4, or 6 hours after administration is beneficial for numerous applications and reduce side effects. Studies suggest that long-term testosterone therapy in hypogonadal men is linked to increased risk of death from cardiovascular disease (Vigen, et al., 2013). Furthermore, the use of testosterone in gel formations has been linked with secondary contamination (de Ronde, 2009).

For administration to a mammal in need of such treatment, the compositions of the present disclosure further comprise one or more excipients appropriate to the indicated route of administration. In some embodiments, the formulation further comprises an excipient such as an agent which enhances the solubility of the pharmaceutically active compound or a carrier which enables the pharmaceutically active compound to cross the blood brain barrier. Excipients that may be used are well and widely known in the pharmaceutical art.

In some embodiments, the pharmaceutical compositions useful in the present disclosure are subjected to conventional pharmaceutical operations such as sterilization and/or further comprise conventional pharmaceutical carriers and excipients such as preservatives, stabilizers, wetting agents, emulsifiers, buffers, etc. In some embodiments, the composition also comprises a preservative. Preservatives which may be used in combination with the pharmaceutical composition of the present invention are known to those of skill in the art. Some preservatives which can be used in the present composition include but are not limited to an antibiotic, an anti-viral agent, antioxidants such as vitamin A, vitamin E, vitamin C, retinyl palmitate, and selenium, amino acids such as methionine and cysteine, citric acid, sodium citrate, or synthetic preservatives such as parabens including methyl paraben and propyl paraben. In some embodiments, the composition of the present disclosure is sterilized. In some embodiments, the composition is sterilized by the filtration. Some filters which can be used for sterilization such as but are not limited to Tuffryn® and Durapore® filter discs. The filter should have pore size of about 20 microns to remove microorganisms such as bacteria. Additionally, a nanofilter is used with a pore size from about 20 to 50 nanometers which will also remove viruses.

The composition describe in this disclosure are administered at a therapeutically effective dosage sufficient to treat a condition in a patient. For example, the efficacy of the compound of the present disclosure can be evaluated in an animal model system that may be predictive of efficacy in treating the disease in humans, such as the model systems shown in the examples and drawings.

The actual dosage amount of the composition of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 50 mg/kg, in one or more dose administrations daily, for one or several days (depending of course on the factors discussed above). In some particular embodiments, the amount is less than 5,000 mg per day with a range of 0.01 mg to 4500 mg per day.

The effective amount may be less than 10 mg/kg/day, less than 50 mg/kg/day, less than 100 mg/kg/day, less than 250 mg/kg/day. It may alternatively be in the range of 0.01 mg/kg/day to 250 mg/kg/day.

In other non-limiting examples, a dose may also comprise from about 0.001 mg/kg/body weight, about 0.01 mg/kg/body weight, about 0.1 mg/kg/body weight, about 5 mg/kg/body weight, or more per administration, and any range derivable therein. In non-limiting examples of a derivable range from the numbers listed herein, a range of about 1 mg/kg/body weight to about 50 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.01% of a testosterone described in the present disclosure. In other embodiments, the compound of the present disclosure may comprise between about 0.1% to about 75% of the weight of the unit, or between about 0.25% to about 60%, or between about 0.25% to about 10%, for example, and any range derivable therein.

Single or multiple doses of the composition of the present disclosure are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day. In other embodiments, the agent is administered more than once a day. In other embodiments, the agent is administered as needed to mitigate the effects of a disease or disorder. In some embodiments, the agent is administered to a patient to treat an acute condition. In other embodiments, the agent is administered to a patient to treat a chronic condition.

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. Thus, for example, the agent can be taken every morning and/or every evening, regardless of when the subject has eaten or will eat.

E. Combination Therapy

In addition to being used as a monotherapy, the composition may also find use in combination therapies. Effective combination therapy may be achieved with a single composition or pharmacological formulation that includes both agents, or with two distinct compositions or formulations, administered at the same time, wherein one composition includes a compound, and the other includes the second agent(s). The other therapeutic modality may be administered before, concurrently with, or following administration of the composition of the present disclosure. The therapy using the composition of the present disclosure may precede or follow administration of the other agent(s) by intervals ranging from minutes to weeks. In embodiments where the other agent and the composition of the present disclosure are administered separately, one would generally ensure that a significant period of time did not expire between the time of each delivery, such that each agent would still be able to exert an advantageously combined effect. In such instances, it is contemplated that one would typically administer the composition of the present disclosure and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a composition of the present disclosure, or the other agent will be desired. In this regard, various combinations may be employed. By way of illustration, where the compounds of the present disclosure are "A" and the other agent is "B", the following permutations based on 3 and 4 total administrations are exemplary:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are likewise contemplated. Non-limiting examples of pharmacological agents that may be used in the present disclosure include other forms of testosterone, another hormone or hormone derivative such as a testosterone derivative, another sex hormone, or cortisol modulating compounds. In some embodiments, the composition of the present disclosure is administered with another form of testosterone such as an intravenous or transdermal dosing of testosterone. In some embodiments, the composition of the present disclosure is administered with an agent that modulates the cortisol levels or the patient's reactivity to cortisol. In some embodiments, the composition of the present disclosure is administered in combination with cortisol.

F. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Formulation of an Aqueous Nasal Testosterone Formulation

A formulation of a testosterone ester was prepared using a combination of water and other additives which would help to solubilize the testosterone in the aqueous environment. The formulation was prepared by combining the testosterone with the first and second additives, Cremophor EL® and Neobee M5®, respectively, with stirring until all components dissolved. Distilled water which has been warmed to a temperature from about 65° C. to about 80° C. is added to the mixture of testosterone, Cremophor EL®, and Neobee M5®. The mixture was then brought to the phase inversion temperature followed by cooling until the mixture is clear. The mixture was be cooled at either ambient room temperature or using an ice bath to achieve clarity. The resulting emulsion was passed through a 0.22 micron Tuffryn® filter and collected in the administration container. The passage through the filter both sterilized the emulsion and imparts more consistency to the droplet size within the emulsion. Without being bound by theory, the filtration of the emulsion and the increased consistency may result in a more consistent kinetic absorption of the drug. The emulsion was then added to a nasal actuator for administration. The resultant emulsion was a nasally administrable testosterone formula containing 1.2% w/w testosterone propionate with 24% w/w Cremophor EL®, 5% w/w Neobee M5®, and 69.8% w/w distilled water. Additionally, a 2.2% w/w testosterone propionate formulation was prepared with 24.8% w/w Cremophor EL®, 14.3% Neobee M5®, and 58.7% w/w distilled water.

If the mixture was not brought to the phase inversion temperature, the resultant mixture did not achieve adequate particle size for administration but does form a translucent emulsion. A variety of different combinations of additives including many different types of oils did not achieve the results obtained in terms of clarity, lack of irritation, or administration ability when using the above additives. For example, ethyl oleate and ethoxy diglycol were used but the resultant mixture was too viscous to produce an aerosol. Additional oils which produced formulations for aerosolization included sesame oil, olive oil, isopropyl myristate, and ethyl oleate. These oils failed for a variety of reasons including but not limited to producing a coarse emulsion rather than a nano emulsion, precipitate of testosterone, sensory intolerability, and viscosity. Without being bound by any theory, it is believed that the concentration of oils such as Cremophor® are important for maintaining a nano emulsion capable of being aerosolized as well as solubilizing the testosterone. Additionally, when higher concentrations of testosterone and other hydrophobic additives are used, the formulation may for a pro-nano emulsion. Without wishing to be bound by any theory, it is believed that when the composition is administered to the nostrils, the composition mixes with nasal fluids and forms a nano emulsion. Additionally, the modification of the concentration of the additional hydrophobic additives, such as Neobee® M-5 or other triglycerides, can affect the solutions viscosity and thus may be used to reduce the compositions ability to drip.

The pharmacokinetic profile of the 2.2% w/w testosterone spray is shown in FIG. 1. The pharmacokinetic profile showed that the peak testosterone concentration for "free", or bioavailable testosterone (the fraction that is considered bioactive and can readily enter cells), (FIG. 1) after approximately 30 minutes. After the peak concentration (476.6%) was achieved at about 30 minutes after administration, the concentration began to reduce such that the concentration has been reduced by about 33% relative to the peak concentration at about 60 minutes. Serum testosterone concentrations were determined by enzyme-linked immunosorbent assay (ELISA) based on the principle of competitive binding, using antibody kits manufactured by DRG International, Inc.

Example 2: Administration of Testosterone to Treat Anxiety and Fear Disorders

Studies illustrated in FIGS. 2-5 showed that testosterone levels are a greater predictive risk factor for post-traumatic stress disorder (PTSD) symptoms than cortisol or cortisol reactivity. The pathogenic nature of cortisol reactivity was completely neutralized when coupled with elevated testosterone levels (see FIG. 5). Statistical analysis of these results show that pre-deployment, low levels of testosterone were pathogenic and strong predictors of increased PTSD symptoms (Tables 1-4). All hormonal predictors were either modeled alongside within-soldier monthly deviations from their own average number of traumatic stressors (PTEWP) or time varying month-to-month traumatic stressor count (PTETV). When modeled together with PTEWP, the effect of average exposure to stressors was interpreted as the total between-soldier effect of having a higher average level of stressor exposure (PTEBP), and when modeled with time-varying stressors (PTETV), the between-soldier effect becomes a contextual or compositional effect, reflecting the effect of having a certain level of overall average stressor exposure, while equating soldiers on month-to-month fluctuations in stressor exposure (PTEComp). This method of explicitly modeling the between-soldier, within-soldier, and compositional components of stressors avoided imposing the problematic assumption that their effects are equal (Hedeker & Gibbons, 2006; Hoffman & Stawski, 2009). Compositional effects that look at between soldier differences, while equating soldiers on the effects of month-to-month stressor fluctuation and the moderating effects of the hormones on the effects of month-to-month stressor fluctuation were utilized for the analysis.

TABLE 1

Statistical Analysis of PTSD Symptoms from Potential Traumatic Warzone Stressors and Cortisol Levels

| PTSD Symptoms | b | se | df | t | p | Significance | Effect Size (r) |
|---|---|---|---|---|---|---|---|
| C × PTEComp | 0.15 | 0.19 | 316.70 | 0.79 | 0.428 | | 0.04 |

TABLE 2

Statistical Analysis of PTSD Symptoms from Potential Traumatic Warzone Stressors and Cortisol Reactivity

| PTSD Symptoms | b | se | df | t | p | Significance | Effect Size (r) |
|---|---|---|---|---|---|---|---|
| CR × PTEComp | 0.03 | 0.19 | 243.50 | 0.17 | 0.869 | | 0.01 |

TABLE 3

Statistical Analysis of PTSD Symptoms from Potential Traumatic Warzone Stressors and Testosterone Levels

| PTSD Symptoms | b | se | df | t | p | Significance | Effect Size (r) |
|---|---|---|---|---|---|---|---|
| T × PTEComp | 0.47 | 0.35 | 230.00 | 2.04 | 0.043 | * | 0.13 |
| PTEComp/Low T | 0.69 | 0.43 | 233.00 | 2.24 | 0.026 | * | 0.15 |
| PTEComp/High T | −0.25 | 0.49 | 216.00 | −0.80 | 0.424 | | 0.05 |

TABLE 4

Statistical Analysis of PTSD Symptoms from Potential Traumatic Warzone Stressors and Testosterone Levels

| PTSD Symptoms | b | se | df | t | p | Significance | Effect Size (r) |
|---|---|---|---|---|---|---|---|
| T × C × PTEComp | −0.71 | 0.26 | 328.20 | −2.73 | 0.007 | ** | 0.15 |
| PTEComp/Low C, Low T | −0.45 | 0.38 | 227.40 | −1.19 | 0.235 | | 0.08 |
| PTEComp/Low C, High T | 0.33 | 0.41 | 274.00 | 0.79 | 0.431 | | 0.05 |
| PTEComp/High C, Low T | 1.43 | 0.45 | 303.30 | 3.16 | 0.002 | ** | 0.18 |
| PTEComp/High C, High T | −0.62 | 0.36 | 339.70 | −1.71 | 0.088 | | 0.09 |

Furthermore, testosterone was found to have great fear reducing effects. Given the relationship between testosterone and PTSD and depressive symptoms described in FIGS. 2-5, the administration of testosterone was shown to lead to reduced symptoms of PTSD and depression. Testosterone levels predicted a fear-based disorder when fear-inducing stimuli are in abundance, such as high number of stressors.

Example 3: The Influence of Endogenous Testosterone on Women's Stress Response to a Performance Stressor Given the debilitating nature of anxiety disorders, a greater understanding of its etiology and the development of appropriate early interventions are critical. Without wishing to be bound by any theory, because testosterone has been implicated in reduction of fear and anxiety, it is believed that women with elevated levels of endogenous testosterone would experience less stress (as measured by cortisol output) when exposed to an intense, acute performance stressor.

A. Procedures 52 female participants were recruited from The University of Texas at Austin Psychology Department SONA participant pool. All participants were scheduled for participation during the estimated luteal phase of their menstrual cycles (between 17$^{th}$ and 28$^{th}$ day following the onset of menstruation) in order to minimize the possible effects of cycling gonadal hormones on the HPA axis. To assess cycle phase, female participants were asked to recall the first day of their most recent menstruation during the telephone screening. Participants currently taking hormonal contraceptives were excluded.

During the study, participants were administered the Trier Social Stress Task, and a total of 7 saliva samples were collected to be analyzed for testosterone and cortisol concentrations.

The standardized Trier Social Stress Task (TSST; Kirschbaum, Pirke, & Hellhammer, 1993) was used to elicit activation of HPA axis. Participants were told that they will be evaluated on their verbal and non-verbal skills (e.g., posture, facial expression, etc.) in an impromptu mock interview by a panel of behavioral experts. Furthermore, they were also instructed that their performances must span five minutes and that their speeches will be video recorded for subsequent in-depth analysis. Participants were given 10 minutes to prepare their presentations. When the five minutes allotted for their speeches elapses, participants were asked to count from 1,022 to 0 in decrements of 13, where they must begin from 1,022 once again if they produce an incorrect response at any point in the sequence.

Upon 30 minutes following arrival, participants were led to another room to prepare for the TSST. Once seated in the preparatory room, participants were asked to drool 2 mL of saliva into a 10 mL cryovial Immediately following this, participants were brought to the TSST room where instructions for the public speaking were provided via a pre-recorded message. Participants were then brought back to the preparatory room and told to prepare for their speech describing why they would be the ideal candidate for a position. After 10 minutes of anticipation, participants provided another salivary sample, and then were administered the TSST. Following the TSST, participants provided a third salivary sample until 4 additional samples were collected. In total, 7 salivary samples were collected.

Salivary testosterone and cortisol concentrations were analyzed in-house with commercially available Salimetrics enzyme immunoassay kits (Salimetrics, State College Pa.). Frozen saliva samples were thawed completely and centrifuged for 10 minutes at 3000 rpm immediately prior to assay. All samples were assayed in duplicate. Hypotheses were tested with using correlations, factorial ANOVAs and independent samples t-tests. All analyses were conducted using PASW Statistics 21.0 for Mac OS X (SPSS, Inc., Chicago Ill.). An alpha level cut-off of 0.05 was used to determine statistical significance.

B. Results

Figure 6:
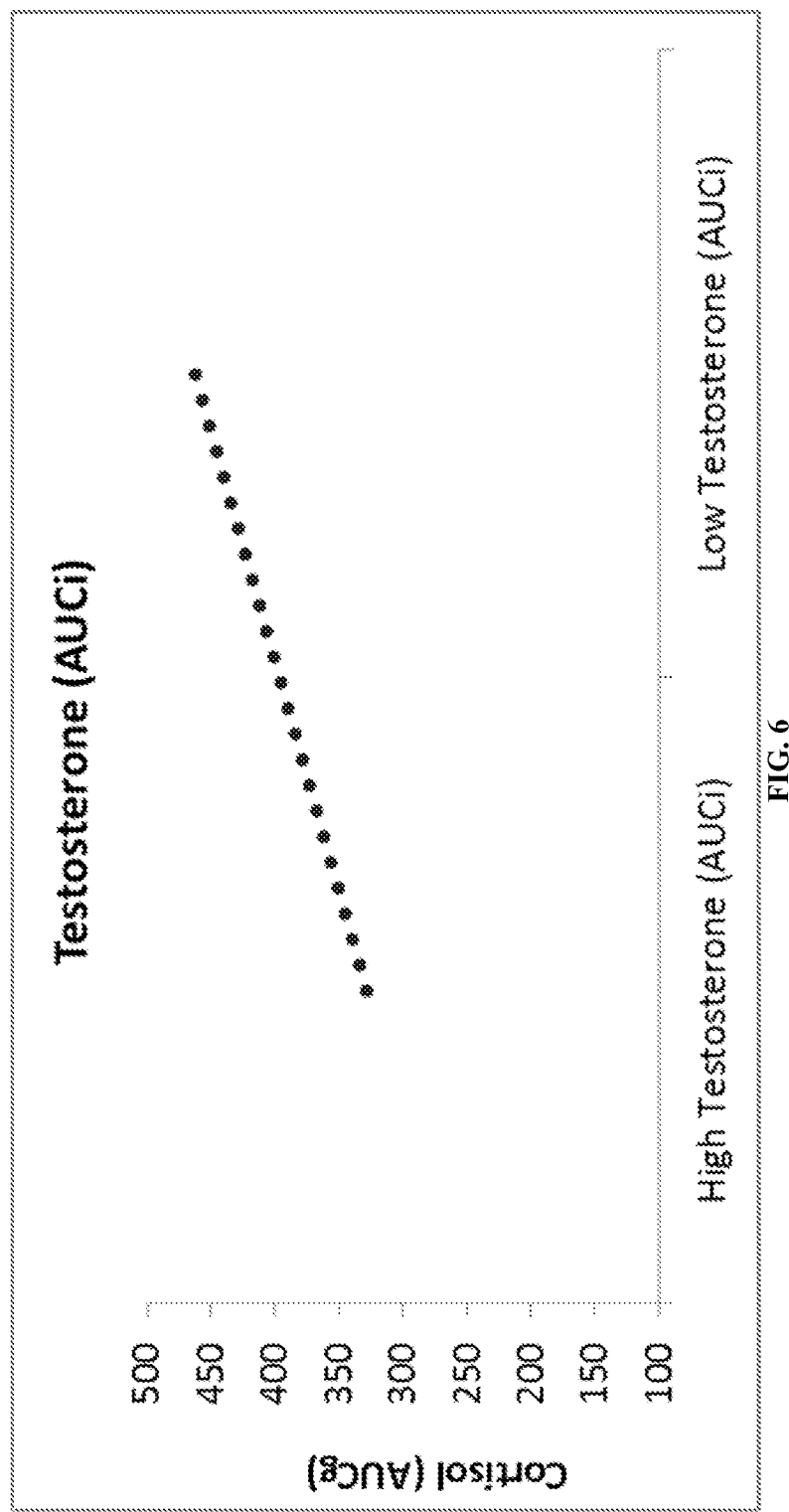
FIG. 6—shows concentration of cortisol as a function of endogenous testosterone concentration. High levels of testosterone showed lower levels of cortisol while low testosterone concentration showed higher levels of cortisol relative to the high testosterone. The data presented in FIG. 6 shows that female participants with higher levels of endogenous testosterone would be relatively immune to the stress-inducing effect of the TSST, resulting in lower levels of cortisol FIG. 7—shows the self reported experiences of patients treated with the aqueous testosterone nasal spray described herein. The patient's reported their experienced energy, libido, anxiety, and irritability levels as well as overall well-being before administration and 30, 60, 120, 180, and 240 minutes post administration. Patients reported increased energy and libido levels as well as increased overall well-being from 30 to 120 minutes post administration as well as decreased levels of anxiety and irritability for the same time period.

Without wishing to be bound by any theory, it is believed that female participants with higher levels of endogenous testosterone would be relatively immune to the stress-inducing effect of the TSST, resulting in lower levels of cortisol. This belief was tested using a linear regression in which total increase in testosterone over the course of the experiment (area under the curve—increase, or AUCi) was used to predict total increase in cortisol. As seen in FIG. 6, the belief was confirmed. Total testosterone was linearly associated with TSST-evoked cortisol accumulation ($p<0.001$), a finding that is consistent with the view that testosterone is protective against stress-inducing environmental threats and traumas.

Prophetic Example 4: Effects of Fast Acting Testosterone Nasal Spray on Young Males Emotional and Behavioral Response to Anxiety The effects of a fast-acting testosterone nasal spray on the fear reactions of young men will be tested. Two distinct anxiety challenges (social and nonsocial) will be used in a double-blind randomized experimental design. The study will determine whether men administered testosterone nasal spray have lower levels of anxiety (anticipatory and situational) and greater levels of approach behavior in response to two distinct (social and nonsocial) anxiety challenges relative to men administered placebo spray. The study will also determine whether the anxiety challenge type (social vs. nonsocial) moderates the effect of testosterone administration on a subject's response to challenge. Finally, the study will determine whether rejection sensitivity (heightened sensitivity to evaluative threat) moderates the effects of drug conditions on response to two anxiety challenge tests.

C. Procedures

The target population for this study will be about eighty men, ages 18-25, with no current medical problems that would preclude the use of testosterone and no current use of testosterone enhancing products.

Data collection will be completed in a single visit to the laboratory, which will last between 2-3 hours. Each subject will be fitted with a chest strap for the recording of heart rate and a wrist strap for the recording of electrodermal response. Salivary testosterone samples will be collected at two different time points: after signing the consent and after completing the pre-challenge battery (30 minutes post nasal spray). Salivary testosterone and cortisol concentrations will be analyzed in-house with commercially available Salimetrics enzyme immunoassay kits (Salimetrics, State College Pa.). Frozen saliva samples will be thawed completely and centrifuged for 10 minutes at 3000 rpm immediately prior to assay. All samples will be assayed in duplicate.

Participants will take part in two distinct anxiety challenges one designed to elicit social anxiety and one designed to elicit non-social anxiety. Each challenge will consist of two phases—an anticipatory phase and a performance phase. Prior to testosterone/placebo administration, participants will complete a computerized Pre-Medication Assessment Battery.

The testosterone spray will consist of 7 mg of testosterone in a solution with 125 mg of 0.5% chlorobutanol in 50 mL saline at approximately pH 5. The placebo spray will be identical to the testosterone spray without the testosterone. Both solutions will be sterilized using a 0.22 micron filter and inserted into a sterile, disposable nasal applicator, which will be coded by condition so that the experimenter and participant are blind to drug condition.

1. Social Anxiety Challenge

The participant will stand in front of a desk, two examiners, and a video camera. The examiners will remain expressionless during the encounter and maintain eye contact with the participant throughout. The experimenter will turn on the recorded message and the instructions for the social anxiety challenge will be played. After the instructions are heard, the experimenter will lead the participant to the preparatory room where they will immediately complete the post-instruction assessment battery. After completing the post-instruction assessment battery, the Experimenter will remind the subject that they have five minutes to prepare for the speech. The Experimenter will leave the room and return after five minutes to escort the participant to the door of the filming room. The experimenter will direct the participant inside the room and close the door from the outside. The participant will be instructed to begin talking until one of the following two conditions is met: (a) 5 min. have elapsed; or (b) the participant chooses to stop the speech before the 5 min. limit. If the participant finishes their speech in fewer than five minutes, the examiner will be quiet for 20 seconds, ask if the participant is finished talking, and if so, will then tell the participant that they are about to do a five minute arithmetic task.

In the arithmetic task, the participant will be told that they are about to do a five minute arithmetic task in which their non-verbal behavior and their arithmetic accuracy will be evaluated. The subject will be asked to serially subtract the number 13 from 1,022 as fast and as accurately as possible. Every time subjects make an error, they will be directed to stop, informing them that they were incorrect and that they need to restart from the beginning and subtract 13 from 1,022. The arithmetic task will end when either a) five minutes has elapsed or b) the participant stops the task. Total speech time will be recorded and will serve as the primary index of behavioral approach. During the course of their speech the participant will be video recorded.

At the completion of the social anxiety challenge, the participant will be escorted back to the testing room and will be administered an "Attribution Questionnaire" along with the "Post-Anxiety Challenge Assessment Battery". Once completed, the participant will be instructed to relax for 5 min before the Claustrophobia Anxiety Challenge.

2. Claustrophobia Anxiety Challenge

Participants will watch a video clip providing instructions. Immediately following the video clip, participants will complete the Post-Instruction Assessment Battery. They will then be escorted to the "claustrophobia room" and given 5 minutes alone to prepare. After the 5 min have elapsed, the participant will be assisted into the chamber and position himself on his back, at which point, the chamber door will be closed and locked. The task will continue until one of the following two conditions is met: (a) 5 min. have elapsed; or (h) the participant chooses to stop the challenge by signaling that he wishes to exit prior to the 5 arm limit.

At the completion of the Claustrophobia Anxiety Challenge, the participant will be escorted back to the testing room and will be administered the "Post-Anxiety Challenge Assessment Battery". After completing both anxiety challenges, the participant will be administered the Debriefing battery.

D. Measures

1. Pre-Medication Assessment Battery

The computerized Pre-Medication Assessment Battery consisting of the following empirically-supported psychometric self-report scales.

Acceptance and Action Questionnaire—This 9-item version of the Acceptance and Action Questionnaire (AAQ; Hayes et al., 2004) is widely used to assess the psychological construct of experiential avoidance. This scale will be used to test experiential avoidance as a putative moderator of the effects of testosterone on anxiety indices.

Trait Anxiety Scale (STAI-T; Spielberger et al., 1983) is a widely used and psychometrically sound 20-item self-report questionnaire designed to assess trait anxiety. This scale will be used to test whether trait anxiety moderates the effects of testosterone on participants' fear response to the two anxiety challenges.

Anxiety Sensitivity Index-3 (ASI-3; Taylor et al., 2007) is a widely used and psychometrically sound 18-item self-report questionnaire designed to assess physical, cognitive and social concerns associated with the fear of anxiety. This scale will be used to test whether the fear of anxiety moderates the effects of testosterone on participants' fear response to the two anxiety challenges.

Social Interaction Anxiety Scale (SIAS; Mattick & Clarke, 1998) is a widely used 20-item scale describing one's reactions to situations involving social interactions. This scale will be used to test whether participants' level of social interaction anxiety moderates the effects of testosterone on participants' fear response to the claustrophobia challenge.

Claustrophobia Concerns Questionnaire (CCQ; Valentiner et al., 1996) was developed to assess the level of entrapment and suffocation concerns that are common factors in the psychopathogenicity of claustrophobia. This scale will be used to test whether the fear of anxiety moderates the effects of testosterone on participants' fear response to the claustrophobia challenge.

Profile of Mood States—Short Form (POMS-SF; Shachman, 1983) is a widely used and psychometrically sound 37-item self-report scale for assessing mood disturbance with individual indices for six different mood states—fatigue, vigor, anxiety, depression, anger, and confusion. This scale will be used to index changes in mood across the different phases of the experimental session.

2. Post-Instruction Assessment Battery

The computerized Post-Instruction Assessment Battery consisting of the following scales.

POMS-SF—See above.

Anticipated Fear (0-100). Global ratings of anticipated (expected) fear will be collected immediately prior to each of the two anxiety challenges to index the effects of testosterone/placebo on participants' perception of their anticipated fear reactivity to the challenge.

Perceived Coping Self-Efficacy (0-100). Global ratings of perceived coping efficacy will be collected immediately prior to each of the two anxiety challenges to index the effects of testosterone/placebo on participants' perception of coping self-efficacy.

3. Post-Challenge Assessment Battery

Participants will complete a computerized assessment battery to index their peak fear, perceived performance, and state mood. Note that this battery will be administered twice (i.e. once after each of the two anxiety challenges). The specific measures will include the following.

POMS-SF—See Above

Peak Fear Rating (0-100) Participants will be asked to rate the highest level of fear they experienced at any point during the anxiety challenge.

Global Performance Rating (0-100)—Participants will be asked to rate their actual performance during the challenge on a scale ranging from 0 (extremely poor performance) to 100 (extremely strong performance).

Behavioral Approach Score (0-300)—The experimenter will record the total duration in seconds that the participant performed the challenge. Note that participants will not be aware of the 300 second performance ceiling.

Body Vigilance Questionnaire—15 item bodily sensation subscales (Schmidt et al. 1997)—The Body Vigilance Scale (BVS) is a measure developed to assess one's conscious attendance to internal cues. The 15 question bodily sensation subscale of Body vigilance questionnaire will be used after each anxiety challenge as measure of participants' anxiety sensitivity. The bodily sensation subscale involves separate ratings for attention to 15 bodily vigilance and anxiety sensations (e.g., heart palpitations) that include all of the DSM IV physical symptoms described far panic attacks in accordance with the Diagnostic and Statistical Manual of Mental Disorders (DSM-IV; American Psychiatric Association, 1994).

Attribution of Performance Social Anxiety Challenge Questionnaire-Attribution of Performance on the Social Challenge will measure with the Attribution of Performance—Social Anxiety Challenge Questionnaire which was created for this study. The questionnaire consists of 5 items which participants respond to on a 7 point Likert scale with 3 of the items assessing how well participants believe they did in comparison to others on the social anxiety challenge and two of the items assessing who they blame for their performance.

4. Debriefing Battery

At the conclusion of the experiment, participants will complete the measures to assess their rumination, their perceived medication assignment and perceived medication effects.

14-item negative thoughts subscale of the Thoughts Questionnaire (Edwards et al., 2003). —State rumination on the social anxiety challenge will be assessed using the 14-item negative thoughts subscale of the Thoughts Questionnaire. Participants will indicate how often they had specific thoughts about the social anxiety challenges, using a 5-point scale, ranging from "never" (0) to "very often" (4). Items will be summed for a total state rumination score.

Perceived Medication Assignment Survey—This two-item survey will assess participants' beliefs about their medication assignment. The first survey item will ask the subject to indicate which medication (testosterone or placebo) they were administered. The second item will index their degree of confidence in their medication assignment using a 0 to 100 point scale.

Medication Effects Form—This 30-item survey assesses possible physical effects of medication over a brief (30 min) time frame. Participants are presented 30 possible symptoms and asked to rate their presence on a 4-point scale ranging from 0—Not present to 3—severe.

Figure 7:
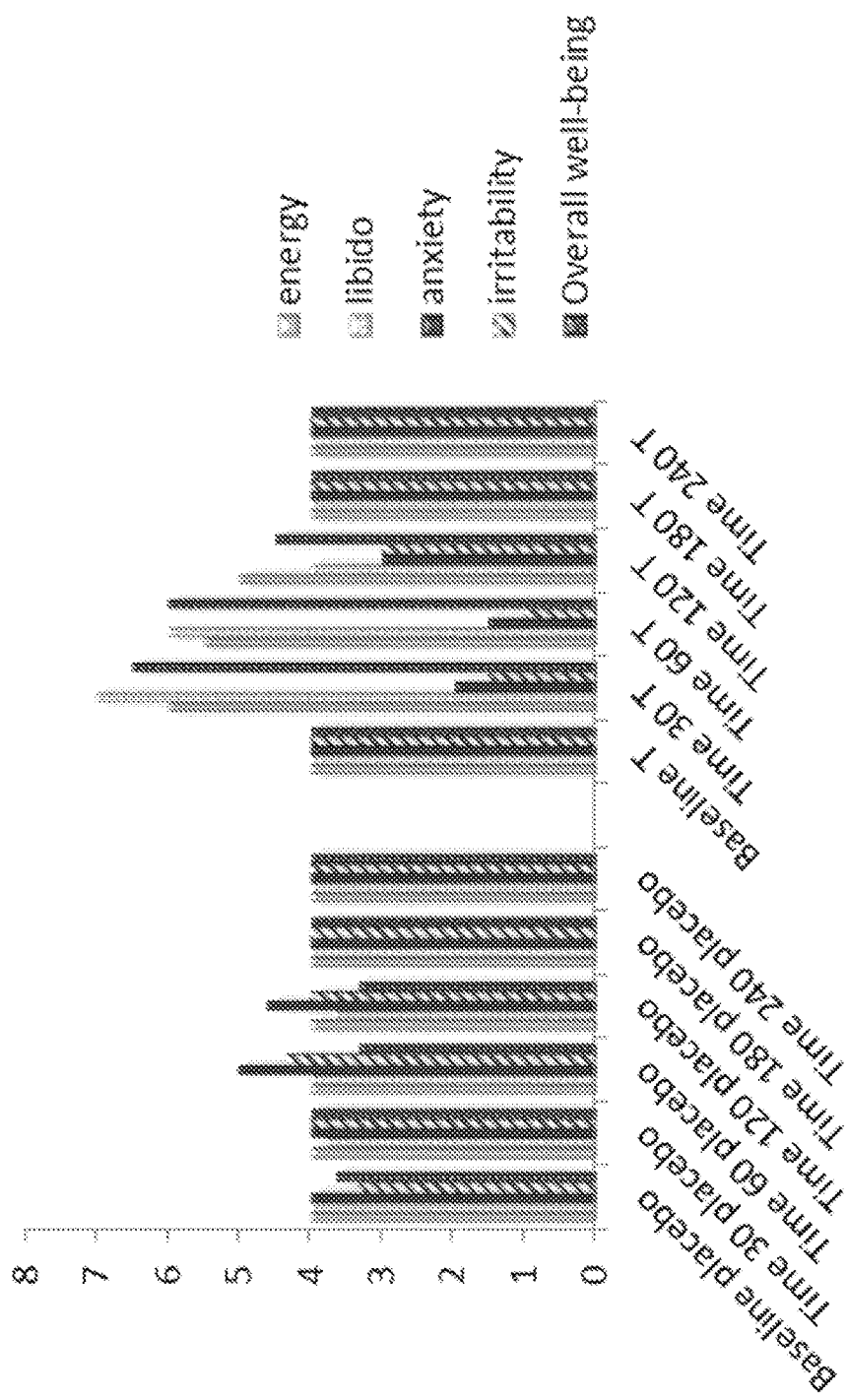

Example 5: Perceived Effects of Fast Acting Testosterone Nasal Spray on Young Males Sexual and Emotional Responses Patients administered with the aqueous testosterone nasal spray described herein reported their perceptions of emotional and sexual state (FIG. 7). Those patients treated with testosterone (N=4) showed increased energy, libido, and overall well being relative to the placebo group (N=3) from 30 minutes post administration to 120 minutes post administration. Similarly, the group treated with the testosterone nasal spray reported decreased experiences of anxiety and irritability relative to the placebo group during that same time period. Data were collected via an online data collection program (Survey Monkey Inc., Palo Alto). Scale values were anchored at 1 and 7, with 1=not at all and 7=extremely high.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

American Psychiatric Association. Diagnostic and statistical manual of mental disorders: DSM-IV 4th ed. Washington (DC): American Psychiatric Association; 1994, p. 866

Banks, et al., Delivery of testosterone to the brain by intranasal administration: comparison to intravenous testosterone, *Journal of Drug Targeting*, 17(2):91-97, 2009.

Beck, et al., *Anxiety disorders and phobias: A cognitive perspective*. Basic Books, 2005.

Davison, et al., Pharmacokinetics and acute safety of inhaled testosterone in postmenopausal women, *The Journal of Clinical Pharmacology*, 45(2):177-184, 2005.

De Ronde, Hyperandrogenism after transfer of topical testosterone gel: case report and review of published and unpublished studies, *Human Reproduction*, 24(2), 425-428, 2009.

Edwards et al., Post-event rumination and recall bias for a social performance event in high and low socially anxious individuals, *Cognitive Therapy and Research*, 27:603-617, 2003.

Giltay, et al., Salivary testosterone: Associations with depression, anxiety disorders, and antidepressant use in a large cohort study, *Journal of psychosomatic research*, 72(3):205-213, 2012.

*Handbook of Pharmaceutical Salts: Properties, and Use* (P. H. Stahl & C. G. Wermuth eds., Verlag Helvetica Chimica Acta, 2002).

Hayes et al., Measuring experiential avoidance: A preliminary test of a working model, *The Psychological Record*, 54:553-578, 2004.

Hedeker & Gibbons, *Longitudinal data analysis*, (Vol. 451), John Wiley & Sons, 2006.

Hoffman & Stawski, Persons as contexts: Evaluating between-person and within-person effects in longitudinal analysis, *Research in Human Development*, 6(2-3):97-120, 2009.

Mattick & Clarke, Development and validation of measures of social phobia scrutiny fear and social interaction anxiety, *Behav. Res. Ther.*, 36(4):455-470, 1998.

Montgomery, et al., Effect of oestrogen and testosterone implants on psychological disorders in the climacteric, *The Lancet*, 329(8528):297-299, 1987.

Reijnen, et al., The Effect of Deployment to a Combat-zone on Testosterone Levels and the Association with the Development of Posttraumatic Stress Symptoms; a Longitudinal Prospective Dutch Military Cohort Study, *Psychoneuroendocrinology*, 2014.

Rolf, C., et al., Pharmacokinetics of a new transdermal testosterone gel in gonadotrophin-suppressed normal men, *European Journal of Endocrinology*, 146(5):673-679, 2002.

Shacham, A shortened version of the Profile of Mood States, *Journal of Personality Assessment*, 47:305-306, 1983.

Spielberger et al., Manual for the State-Trait Anxiety Inventory, Palo Alto, Calif.: Consulting Psychologists Press, 1983.

Taylor et al., Robust Dimensions of Anxiety Sensitivity: Development and Initial Validation of the Anxiety Sensitivity Index-3, *Psychological Assessment*, 19:176-188, 2007.

Tuiten, et al., Time Course of Effects of Testosterone Administration on Sexual Arousal in Women, *Arch. Gen. Psychiatry*, 57:149-153, 2000.

Valentiner et al., Cognitive mechanisms in claustrophobia: An examination of Reiss and McNally's expectancy model and Bandura's self-efficacy theory, *Cognitive Therapy and Research*, 20:593-612, 1996.

Vigen, et al., Association of testosterone therapy with mortality, myocardial infarction, and stroke in men with low testosterone levels, *J. Am. Med. Assc.*, 310(17), 1829-1836, 2013.

What is claimed is:

1. A pharmaceutical composition comprising:
   (A) a testosterone ester$_{(C \leq 12)}$,
   (B) water, wherein the water comprises from about 50% to about 90% of the composition by weight,
   (C) a first additive, wherein the first additive is a reaction mixture from the reaction of castor oil with ethylene oxide, and
   (D) a second additive, wherein the second additive is a caprylic/capric triglyceride.

2. The composition of claim 1, wherein the testosterone ester$_{(C \leq 12)}$ is testosterone propionate.

3. The composition of claim 1, wherein the reaction comprises a molar ratio of ethylene oxide to castor oil of about 35:1.

4. The composition of claim 1, wherein the second additive comprises from about 1% to about 10% by weight of the composition.

5. The composition according of claim 1, wherein the second additive comprises from about 10% to about 20% by weight of the composition.

6. The composition of claim 1, wherein the testosterone ester$_{(C \leq 12)}$ comprises from about 0.1% to about 5% by weight of the composition.

7. The composition of claim 1, wherein the water comprises from about 65% to about 75% by weight of the composition.

8. The composition of claim 1, wherein the water comprises from about 55% to about 65% by weight of the composition.

9. The composition of claim 1, wherein the first additive comprises from about 15% to about 26% by weight of the composition.

10. A pharmaceutical composition comprising about 1.2% by weight testosterone propionate, about 69.8% by weight distilled water, about 5.0% by weight of a medium chain triglyceride with the CAS Registry No. 73398-61-5, and about 24% by weight of a polyethoxylated caster oil with the CAS Registry No. 61791-12-6 or about 2.2% by weight testosterone propionate, about 58.7% by weight distilled water, about 14.3% by weight of a medium chain triglyceride with the CAS Registry No. 73398-61-5, and about 24.8% by weight of a polyethoxylated caster oil with the CAS Registry No. 61791-12-6.

11. A method of treating a testosterone deficiency disease or disorder in a patient in need thereof comprising nasally administering to the patient a therapeutically effective amount of a composition of claim 1.

12. The method of claim 11, wherein the disease or disorder is a disease or disorder associated with fear and anxiety.

13. The method of claim 12, wherein the disease or disorder is a disorder of the fear processing system.

14. The method of claim 11, wherein the deficiency in testosterone leads to decreased libido.

15. The method of claim 11, wherein the patient has erectile dysfunction.

* * * * *